United States Patent [19]

Abou-Gharbia et al.

[11] Patent Number: 4,988,814
[45] Date of Patent: Jan. 29, 1991

[54] TERTIARY ALKYL FUNCTIONALIZED PIPERAZINE DERIVATIVES

[75] Inventors: Magid A. Abou-Gharbia, Glen Mills; John P. Yardley, Gulph Mills, both of Pa.; Ian A. Cliffe, Slough, United Kingdom

[73] Assignees: American Home Products Corp., New York, N.Y.; John Wyeth & Bro., Maidenhead, England

[21] Appl. No.: 428,148

[22] Filed: Oct. 27, 1989

[30] Foreign Application Priority Data

Apr. 22, 1989 [GB] United Kingdom ............... 8909209

[51] Int. Cl.$^5$ ................... C07D 403/04; C07D 401/04
[52] U.S. Cl. ..................... 544/295; 544/357; 544/360; 544/392; 544/393; 544/394
[58] Field of Search ............... 544/295, 357, 360, 392, 544/393, 394

[56] References Cited

U.S. PATENT DOCUMENTS

| | | | |
|---|---|---|---|
| 4,001,223 | 1/1977 | Sugimoto et al. | 544/380 |
| 4,202,898 | 5/1980 | Depoortere | 544/394 |
| 4,510,140 | 4/1985 | Nardi et al. | 544/360 |
| 4,605,655 | 8/1986 | Yevich et al. | 544/295 |
| 4,873,331 | 10/1989 | Childers, Jr. et al. | 544/295 |
| 4,880,930 | 11/1989 | New | 544/295 |
| 4,882,432 | 11/1989 | Abou-Gharbia et al. | 544/393 |

FOREIGN PATENT DOCUMENTS

| | | |
|---|---|---|
| 814287 | 10/1974 | Belgium . |
| 0048045 | 3/1982 | European Pat. Off. . |
| 0318933 | 6/1989 | European Pat. Off. . |
| 2432516 | 2/1980 | France . |
| 81167 | 5/1985 | Japan ................ 544/295 |

OTHER PUBLICATIONS

Depoortere, Chem. Abst. 93-186411b (1980).
Synthelabo S. A. Chem. Abst. 93-26461w (1980).
Najer et al., Chem. Abst. 93-150280a (1980).
Haeck et al., Chem. Abst. 97-38956g (1982).

*Primary Examiner*—Cecilia Shen
*Attorney, Agent, or Firm*—R. K. Jackson

[57] ABSTRACT

Compounds of the formula:

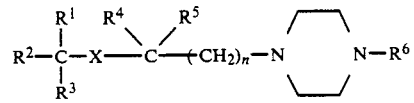

in which $R^1$ is alkyl; $R^2$ and $R^3$ are alkyl or taken together they are polymethylene, $R^2$ and $R^3$ complete a 5-norbornen-2-yl moiety; X is —CO$_2$—, —OCO—, —OCO$_2$—, —N(R$^7$)CO—, —NHNHCO—, —ON(R$^7$)CO—, —CON(R$^7$)—, —N(R$^7$)CO$_2$—, —OCON(R$^7$)— or —N(R$^7$)CON(R$^8$)—, wherein $R^7$ and $R^8$ are, independently, hydrogen, alkyl, phenyl, benzyl, substituted phenyl or substituted benzyl in which the substituents are halo, alkyl alkoxy, cyano, nitro or perhalomethyl; $R^4$ is hydrogen or alkyl; $R^5$ is hydrogen, alkyl, hydroxyalkyl, phenyl, benzyl, substituted phenyl or substituted benzyl in which the substituents are hydroxy, halo, alkyl alkoxy, trifluoromethyl, nitro, cyano, carbalkoxy, carboxamido, amino, alkylamino or dialkylamino; $R^6$ is phenyl, benzyl, 2-, 3-, or 4-pyridinyl, 2-pyrimidinyl or 2-pyrazinyl any of which may be substituted by one or more hydroxy, halo, alkyl alkoxy, trifluoromethyl, nitro, cyano, carbalkoxy, carboxamido, amino, alkylamino or dialkylamino; n is one of the integers 0, 1, 2, 3, 4 or 5; or a pharmaceutically acceptable salt thereof, with the proviso that when X is —CON(R$^7$)— and R$^7$ is alkyl, R$^6$ is other than 2-pyrimidinyl, and when X is —CO$_2$— and $R^1$, $R^2$ and $R^3$ are methyl and n is 1, R$^6$ is other than 3,5-di(trifluoromethyl)phenyl are antidepressant and/or anxiolytic agents.

37 Claims, No Drawings

TERTIARY ALKYL FUNCTIONALIZED PIPERAZINE DERIVATIVES

RELATED APPLICATIONS

U.S. patent application Nos. 335,075; 297,509 and 294,853 disclose adamantyl and noradamantyl piperazine amides, carbamates, carbonates and ureas with high $5HT_{1A}$ affinitives. These compounds, as well as those disclosed in U.S. Pat. No. 4,797,489 by Abou-Gharbia et al. are useful for treatment of CNS disorders.

BACKGROUND OF THE INVENTION

The anxiolytic activity of buspirone and structurally related compounds has been attributed to their selective activity at a serotonin (5-hydroxytyptamine; 5-HT) subtype receptor designated the $5\text{-}HT_{1A}$ receptor. U.S. Pat. No. 4,202,898 discloses the treatment of anxiety and depression with a group of substituted phenylpiperazine derivatives. Among the compounds disclosed as useful for that purpose is 2,2-dimethylpropanoic acid (3-trifluoromethylthio phenyl-piperazino)ethyl ester (column 3, compound 21). The therapeutic value of $5\text{-}HT_{1A}$ receptor agonists in treating multi-CNS disorders has recently been extended to compound structures such as umespirone which has high affinity for both the $5\text{-}HT_{1A}$ and $D_2$ receptor binding sites (E.P. DE No. 3529872, 87/9).

DESCRIPTION OF THE INVENTION

In accordance with this invention there is provided a group of novel compounds which exhibit serotonin $5HT_{1A}$ receptor affinity which characterizes them as antidepressant and/or anxiolytic agents. Some of the compounds of this invention exhibit both $5HT_{1A}$ receptor affinity and dopamine $D_2$ receptor binding which characterizes them as anxiolytic and/or antidepressant agents with elements of antipsychotic activity. The compounds of this invention are of the following structural formula:

$$R^2-\underset{\underset{R^3}{|}}{\overset{\overset{R^1}{|}}{C}}-X-\overset{R^4}{\underset{}{C}}\diagdown\diagup\overset{R^5}{}-(CH_2)_n-N\diagup\diagdown N-R^6$$

in which $R^1$ is alkyl of 1 to 6 carbon atoms;

$R^2$ and $R^3$ are alkyl of 1 to 6 carbon atoms or taken together they are polymethylene of 2 to 12 carbon atoms or taken together with the carbon atom to which they are attached, $R^2$ and $R^3$ complete a 5-norbornen-2-yl moiety;

X is $-CO_2-$, $-OCO-$, $-OCO_2-$, $-N(R^7)CO-$, $-NHNHCO-$, $-ON(R^7)CO-$, $-CON(R^7)-$, $-N(R^7)CO_2-$, $-OCON(R^7)-$ or $-N(R^7)CON(R^8)-$; wherein $R^7$ and $R^8$ are, independently, hydrogen, alkyl of 1 to 6 carbon atoms, phenyl, benzyl, substituted phenyl or substituted benzyl in which the substituents are halo, alkyl of 1 to 6 carbon atoms, alkoxy of 1 to 6 carbon atoms, cyano, nitro or perhalomethyl;

$R^4$ is hydrogen or alkyl of 1 to 6 carbon atoms;

$R^5$ is hydrogen, alkyl of 1 to 8 carbon atoms, hydroxyalkyl of 1 to 3 carbon atoms, phenyl, benzyl, substituted phenyl or substituted benzyl in which the substituents are hydroxy, halo, alkyl of 1 to 6 carbon atoms, alkoxy of 1 to 6 carbon atoms, trifluoromethyl, nitro, cyano, carbalkoxy of 2 to 7 carbon atoms, carboxamido, amino, alkylamino of 1 to 6 carbon atoms or dialkylamino of 2 to 12 carbon atoms;

$R^6$ is phenyl, benzyl, 2-, 3-, or 4-pyridinyl, 2-pyrimidinyl or 2-pyrazinyl; any of which may be substituted by one or more hydroxy, halo, alkyl of 1 to 6 carbon atoms, alkoxy of 1 to 6 carbon atoms, trifluoromethyl, nitro, cyano, carbalkoxy of 2 to 7 carbon atoms, carboxamido, amino, alkylamino of 1 to 6 carbon atoms or dialkylamino of 2 to 12 carbon atoms;

and n is one of the integers 0, 1, 2, 3, 4 or 5; or a pharmaceutically acceptable salt thereof, with the proviso that when X is $-CON(R^7)-$ and $R^7$ is alkyl, $R^6$ is other than 2-pyrimidinyl and when X is $-CO_2-$ and $R^1$, $R^2$ and $R^3$ are methyl and n is 1, $R^6$ is other than 3,5-di(trifluoromethyl)phenyl.

The preferred compounds from the standpoint of production economics and activity profile are those of the formula:

$$R^2-\underset{\underset{R^3}{|}}{\overset{\overset{R^1}{|}}{C}}-X-\overset{R^4}{\underset{}{C}}\diagdown\diagup\overset{R^5}{}-(CH_2)_n-N\diagup\diagdown N-R^6$$

$R^1$ is alkyl of 1 to 6 carbon atoms;

$R^2$ and $R^3$ are alkyl of 1 to 6 carbon atoms or taken together they are polymethylene of 2 to 6 carbon atoms or taken together with the carbon atom to which they are attached, $R^2$ and $R^3$ complete a 5-norbornen-2-yl moiety;

X is $-CO_2-$, $-OCO-$, $-OCO_2-$, $-N(R^7)CO-$, $-NHNHCO-$, $-ON(R^7)CO-$, $-CON(R^7)-$, $-N(R^7)CO_2-$, $-OCON(R^7)-$ or $-N(R^7)CON(R^8)-$; wherein $R^7$ and $R^8$ are, independently, hydrogen, alkyl of 1 to 6 carbon atoms, phenyl, benzyl, substituted phenyl or substituted benzyl in which the substituents are halo, alkyl of 1 to 6 carbon atoms, alkoxy of 1 to 6 carbon atoms, cyano, nitro or perhalomethyl;

$R^4$ is hydrogen or alkyl of 1 to 6 carbon atoms;

$R^5$ is hydrogen, alkyl of 1 to 6 carbon atoms, hydroxyalkyl of 1 to 3 carbon atoms, phenyl, benzyl, p-hydroxyphenyl, p-methoxyphenyl, o-methoxyphenyl, p-chlorophenyl or p-fluorophenyl;

$R^6$ is phenyl, 2-alkylphenyl in which the alkyl substituent has 1 to 6 carbon atoms, 2-alkoxyphenyl in which the alkoxy substituent has 1 to 6 carbon atoms, 2-halophenyl, 2-cyanophenyl, 2-nitrophenyl, 2-perhalomethylphenyl, benzyl, 2-, '3-, or 4-pyridinyl, 2-pyrimidinyl or 2-pyrazinyl;

and n is one of the integers 0, 1, 2, 3, 4 or 5; or a pharmaceutically acceptable salt thereof, with the proviso that when X is $-CON(R^7)-$ and $R^7$ is alkyl, $R^6$ is other than 2-pyrimidinyl.

The halo substituent referred to in the preceding paragraph may be chloro-, bromo-, fluoro- or iodo, the chloro-, bromo- and fluoro- substituents being preferred. For simplicity, the lower alkyl and alkoxy groups containing 1 to 4 carbon atoms are preferred throughout the molecules. The pharmaceutically acceptable salts are produced conventionally from such acids as hydrochloric, hydrobromic, sulfuric, phosphoric, methane sulfonic, nitric, p-toluene sulfonic, acetic, citric, maleic, succinic acid and the like.

The compounds of this invention present chiral centers depending upon the substituent variations of $R^1$, $R^2$ and $R^3$ and $R^4$ and $R^5$. The optical isomers generated at these positions may be separated and isolated or directly produced from reactants of known or related configurations, by conventional means.

Highly selective $5HT_{1A}$ receptor binding has been observed with the compounds of this invention in which $R^5$ is alkyl of 4 to 8 carbon atoms or an optionally substituted phenyl or benzyl moiety. These compounds demonstrate only poor relative binding to the $D_2$ and $\alpha_1$ receptors. As such, their selective anxiolytic activity is clearly indicated.

The compounds of this invention are produced by various conventional methods from commercially available starting materials or reactants producible by conventional techniques. Thus, for example, the desired tertiary butyl ureas, carbamates, and carbonates can be prepared by reacting tert-alkylamine or tert-alkylalcohol with the appropriate piperazinylalkanol or piperazinylalkylamine in the presence of phosgene or an appropriate phosgene equivalent such as trichloromethyl chloroformate in a suitable solvent such as methylene chloride, thusly,

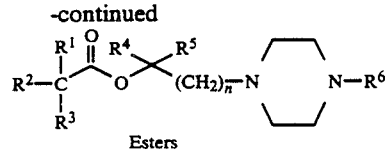
Esters

The desired α-substituted carboxamides can be prepared by reacting the appropriately substituted N-benzylpiperazinylalkylamine with an acid halide in methylene chloride and in the presence of triethylamine to afford the N-benzylcarboxamide intermediate, which is debenzylated and substituted with the appropriate aryl- or heteroarylhalide, thusly:

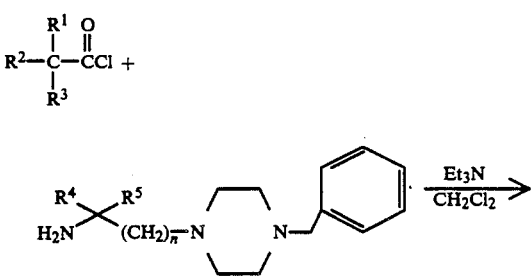

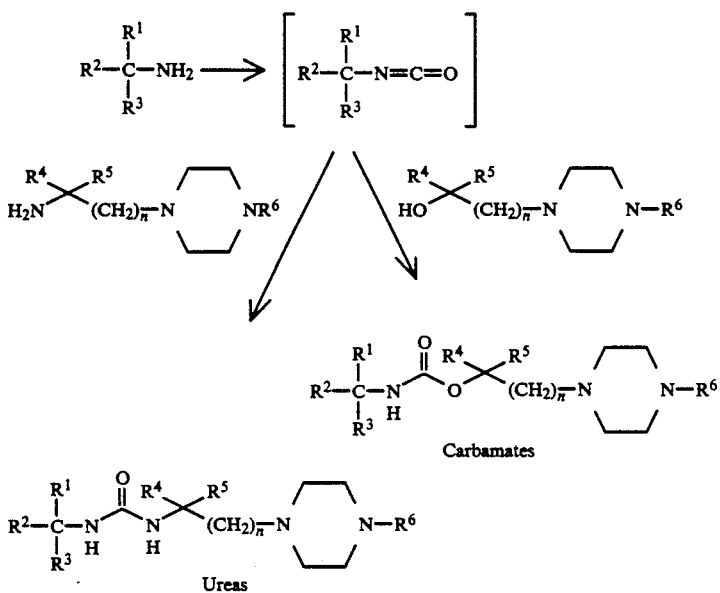
Carbamates

Ureas

The desired esters are prepared by reaction of the appropriately substituted piperazinylalkanol with an acid halide in a suitable solvent such as $CH_2Cl_2$ in the presence of an acid acceptor such as triethylamine.

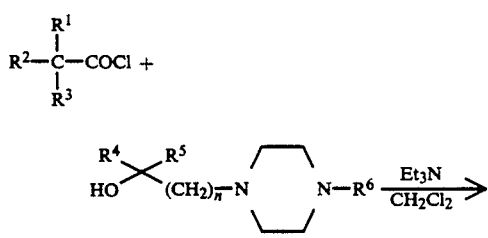

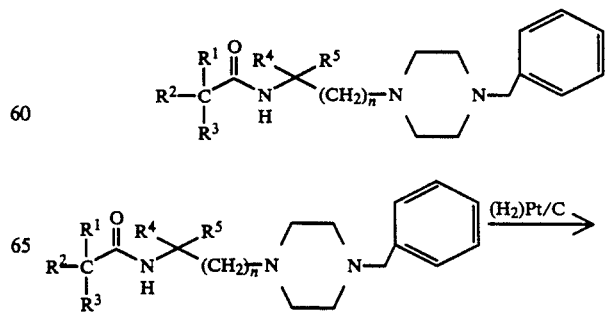

-continued

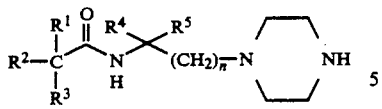

Et₃N, DMF
Cl—R⁶

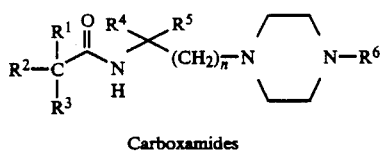

Carboxamides

Of course, the reverse esters, amides and carbamates are prepared in the same manner with the oppositely functional reactants.

For example, in one method for preparing the reverse amide (in which X is —NR⁷CO—) an amine or the formula:

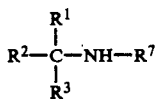

is acylated with an acid of the formula:

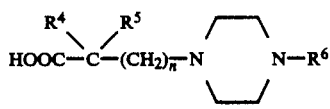

or with any acylating derivative thereof. Examples of acylating derivatives include the acid halides (e.g. acid chlorides), azides, anhydrides, imidazolides (e.g. obtained from carbonyldiimidazole), activated esters or O-acyl ureas obtained from a carbodiimide such as a dialkylcarbodiimide particularly dicyclohexylcarbodiimide. Preferably the amine is acylated with the acid in presence of a coupling agent such as 1,1'-carbonyldiimidazole, iso-butylchloroformate or diphenylphosphinyl chloride. The hydrazides and hydroxamates are produced in the same manner from the substituted hydrazine or substituted hydroxylamine and the desired carboxylic acid. A reverse ester of the invention (i.e. a compound where X is —OCO—) may be prepared by esterification of the above acid with an alcohol of the formula:

Esterification may be carried out by the general methods known in the art.

An alternative method of preparing the compounds of the invention comprises alkylation of a piperazine of the formula:

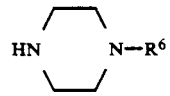

with an alkylating agent providing the group:

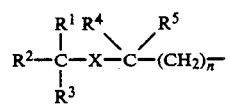

The alkylating agent may be, for example, a compound of the formula:

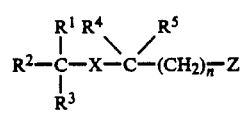

where Z is a leaving group such as halogen or an alkyl- or aryl-sulphonyloxy group. Alternatively where n is 1 the alkylating agent may be an unsaturated compound of the formula:

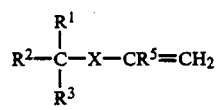

and the compounds are reacted by means of a Michael reaction. The reaction may be carried out at elevated temperature in the presence of an alcohol.

The amides of the invention in which X is —NH—CO— may be prepared by an alternative method comprising reacting a nitrile of the formula:

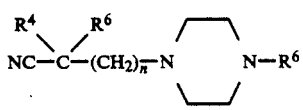

with the tertiary alcohol of the formula:

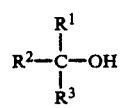

under acidic conditions as in the Ritter reaction.

A further method of preparing the reverse amides of the invention in which n is 1 comprises the desulphurisation of a sulphur containing compound of the formula:

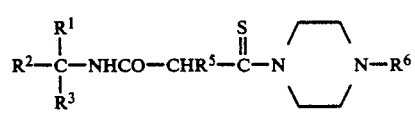

The desulphurisation may be carried out in the presence of a nickel catalyst. The sulphur containing compound may be prepared by a Willgerodt reaction, e.g. an aryl alkyl ketone of the formula CH₃CO—R⁵ is reacted with sulphur and a piperazine of the formula:

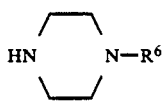

and the resulting thioamide is treated with a base and with an isocyanate of the formula:

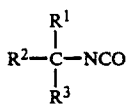

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

The following Examples illustrate, without limitation, the preparation of representation compounds of this invention.

EXAMPLE 1

N-(1,1-Dimethylethyl)-N¹-[4-[4-(2-methoxyphenyl)-1-piperazinyl]butyl]urea

To a suspension of tert-butylamine (0.4 g, 0.005 mol) in 50 mL of dry methylene chloride under a dry nitrogen atmosphere was added triethylamine (1.2 g, 0.01 mol). The resulting solution was refluxed for thirty minutes, and then trichloromethyl chloroformate (0.57 g, 0.002 mol) was added dropwise via syringe and the resulting suspension was refluxed for three hours. The reaction mixture was then allowed to cool to room temperature, and to the cold solution was added a solution of 2-[4-(2-methyoxyphenyl)-1-piperazinyl]butylamine (1.5 g, 0.005 mol) in 15 mL of dry methylene chloride, followed by an additional two equivalents of triethylamine (1.2 g, 0.01 mol). The resulting mixture was allowed to stir at room temperature overnight. The reaction mixture was diluted to 200 mL with methylene chloride, washed with 5% aqueous sodium bicarbonate solution, dried over anhydrous sodium sulfate, and concentrated on a rotary evaporator to a yellow oil. The desired product (TLC on silica gel using a 20% methanol in ethyl acetate solvent mixture, Rf=0.41) was isolated by gravity chromatography on silica gel and converted to the hydrochloride salt to afford 0.33 g of the title compound as a trihydrochloride, mp.=167°-169° C.

Elemental analysis for $C_{20}H_{34}N_4O_2 \cdot 3HCl$

Calc'd: C, 50.90; H, 7.90; N, 11.87
Found: C, 51.04; H, 8.04; N, 11.75

EXAMPLE 2

N-[4-[4-(2-Methoxyphenyl)-1-piperazinyl]butyl]-2,2-dimethylpropanamide

To a stirred solution of 4-(2-methoxyphenyl)-1-piperazinylbutanamine (1.71 g, 0.006 mol) and triethylamine (0.8 g, 0.008 mol) in 50 mL of methylene chloride, pivaloyl chloride (0.78 g, 0.006 mol) was added and stirring was continued overnight at room temperature. The methylene chloride solution was washed with water, dried over anhydrous MgSO₄, and evaporated under reduced pressure. The desired product was isolated by high pressure liquid chromatography (HPLC) on silica gel (using a gradient consisting of from 10% ethyl acetate in hexane to 10% methanol in ethyl acetate) and converted to the dihydrochloride salt (0.95 g, 38%), mp.=191°-196° C.

Elemental analysis for $C_{20}H_{33}N_3O_2 \cdot 2HCl \cdot \tfrac{1}{2}H_2O$

Calc'd: C, 55.94; H, 8.22; N, 9.79
Found: C, 56.03; H, 8.24; N, 9.89

EXAMPLE 3

2,2-Dimethylpropanoic acid 2-[4-(2-methoxyphenyl)-1-piperazinyl]ethyl ester

Piraloyl chloride (15.0 g, 0.124 mol) and triethylamine (13.1 g, 0.13 mol) were stirred with 1-bromoethanol (15.5 g, 0.124 mol) in CH₂Cl₂ at room temperature. The desired product, 2-bromoethylpivalate was recovered for use in the following procedure.

To a stirred solution of N-(2-methoxyphenyl)piperazine (3.64 g, 0.019 mol) and triethylamine (6 g, 0.06 mol) in 80 mL of DMF was added 2-bromoethylpivalate (4 g, 0.019 mol). The reaction mixture was stirred overnight at room temperature. The DMF was removed under reduced pressure and the residue was dissolved in 100 mL of methylene chloride. The organic layer was washed with water, dried (anhydrous Na₂SO₄) and evaporated. The desired product was separated by preparative HPLC and converted to the dihydrochloride salt, mp.=193°-195° C.

Elemental analysis for $C_{18}H_{28}N_2O_3 \cdot 2HCl$

Calc'd: C, 54.96; H, 7.63; N, 7.12; Cl, 18.07
Found: C, 54.94; H, 7.52; N, 6.97; Cl, 17.69

EXAMPLE 4

2,2-Dimethylpropanoic acid 3-[4-(2-methoxyphenyl)-1-piperazinyl]propyl ester

To a stirred solution of 3-[4-(2-methoxyphenyl)-1-piperazinyl]propanol (4.76 g, 0.019 mol) and triethylamine (6 g, 0.06 mol) in 100 mL of methylene chloride was added pivaloyl chloride (2.28 g, 0.019 mol) and stirring was continued overnight at room temperature. The organic layer was washed with water, dried (anhydrous Na₂SO₄) and evaporated. The title compound was isolated by preparative HPLC and converted to the dihydrochloride salt; mp.=202°-204° C.

Elemental analysis for $C_{19}H_{30}N_2O_3 \cdot 2HCl$

Calc'd: C, 56.01; H, 7.86; N, 6.87
Found: C, 56.13; H, 8.09; N, 6.73

EXAMPLE 5

2,2-Dimethylpropanoic acid 3-[4-(2-chlorophenyl)-1-piperazinyl]propyl ester

The title compound was prepared following procedure of Example 4 with the exception that 3-[4-(2-chlorophenyl)-piperazine]propanol (4.89 g, 0.019 mol) was used instead of 3-[4-(2-methoxyphenyl)-piperazinyl]propanol. The title compound was converted to the hydrochloride salt, mp.=186°-188° C.

Elemental analysis for $C_{18}H_{27}N_2O_2 \cdot HCl$

Calc'd: C, 57.06; H, 7.46; N, 7.46
Found: C, 57.73; H, 7.06; N, 7.13

EXAMPLE 6

2,2-Dimethylpropanoic acid 3-[4-(2-pyrimidinyl)-1-piperazinyl]propyl ester

Pivaloyl chloride (15.0 g, 0.124 mol) and triethylamine (13.1 g, 0.13 mol) were stirred with 1-bromopropanol (17.3 g, 0.124 mol) in $CH_2Cl_2$ at room temperature. The desired product, 3-bromopropylpivalate was recovered for use in the following procedure.

To a stirred solution of N-(2-pyrimidinyl)piperazine dihydrochloride (4.25 g, 0.0179 mol) and triethylamine (6.06 g, 0.06 mol) in DMF was added 3-bromopropyl pivalate (4.0 g, 0.0179 mol) and the solution was stirred overnight at room temperature. The solvent was evaporated and the residue dissolved in $CH_2Cl_2$. The $CH_2Cl_2$ extract was washed with water, dried (anhydrous $Na_2SO_4$) and evaporated to afford 9.0 g of crude title compound. Purification by HPLC and conversion to the dihydrochloride with ethereal HCl yielded the product, mp. 178°-180° C.

Elemental analysis for $C_{16}H_{26}N_4O_2 \cdot 2HCl \cdot H_2O$

Calc'd: C, 48.36; H, 7.55; N, 14.10
Found: C, 48.00; H, 7.08; N, 13.70

EXAMPLE 7

(R)-N-[1-Methyl-2-[4-(2-methoxyphenyl)-1-piperazinyl]ethyl] trimethylacetamide To a chilled solution of t-butoxycarbonyl D-alanine (9.45 g, 0.05 mol) and 1-(2-methoxyphenyl)piperazine (9.6 g, 0.05 mol) in 125 mL of $CH_2Cl_2$ was added diethyl cyanophosphonate (8.34 mL, 0.055 mol) in 50 mL of $CH_2Cl_2$ over 30 minutes followed by triethylamine (7.37 mL, 0.055 mol) in 50 mL of $CH_2Cl_2$ over 15 minutes. After 2.5 hour, the solution was washed with water (2×100 mL) and $K_2CO_3$ (2 c 100 mL of 10% aqueous), dried over anhydrous $K_2CO_3$ and evaporated to an oil. The crude 1-(t-butoxycarbonyl-D-alanyl)-4-(2-methoxyphenyl)piperazine was stirred in 200 mL of 4.5N HCl in ethyl acetate for 1 hour at room temperature, diluted with 400 mL of anhydrous diethyl ether, filtered, washed and dried in vacuo. The 1-(D-alanyl)-4-(2-methoxyphenyl)piperazine dihydrochloride was stirred in 200 mL of anhydrous THF, treated with 225 mL of 1M $BH_3$ in THF, and refluxed 3.5 hours. After cooling in ice, the reaction was quenched with 140 mL of 2N aqueous HCl and refluxed 18 hours. THF was removed on a Rotovapor ®, the aqueous solution was made basic with 6N sodium hydroxide and the amine was extracted into diethyl ether. The ether solution was dried over anhydrous $K_2CO_3$, filtered and acidified with 4.5N HCl in ethyl acetate. The salt was filtered, washed with diethyl ether, converted to the free base in 2N NaOH and extracted into diethyl ether. After drying as above and evaporation, the (R)-1-methyl-2-[4-(2-methoxyphenyl)piperazinyl]-ethylamine was obtained as an oil (11.8 g, 94.7% based on BoC-D-alanine). A sample was converted to the trihydrochloride sesquihydrate, mp. 219°-221° C.; $[\alpha]D^{25} = -26.4$ c=0.99 MeOH. $^1$H NMR (DMSO-$d_6$) δ: 1.32 (d, 3H), 3.8 (s, 3H), 6.9-7.0 (m, 4H), IR was devoid of carbonyl peaks.

Elemental analysis for $C_{14}H_{23}N_3O \cdot 3HCl \cdot 1.5 H_2O$)

Calc'd: C, 43.59; H, 7.58; N, 10.89
Found: C, 43.47; H, 7.08; N, 10.57

(R)-[1-methyl-2-[4-(2-methoxyphenyl)-1-piperazinyl]ethylamine (2.49 g, 0.01 mol) and trimethylacetic acid (2.04 g, 0.02 mol) in 25 mL of $CH_2Cl_2$ were chilled in ice and treated with diethylcyanophosphonate (3.26 g, 3.1 mL, 0.02 mol) in 10 mL of $CH_2Cl_2$ over 15 minutes followed by N-methylmorpholine (2.02 g, 2.2 mL, 0.02 mol) in 10 mL $CH_2Cl_2$ over 15 minutes and the reaction was followed by TLC. The reaction was essentially complete after 2 hours. After stirring overnight, the solution was washed with 2N NaOH (2×50 mL), and water (2×50 mL) and dried (anhydrous $K_2CO_3$). The product was isolated using dry column chromatography on silica gel (300 g) and development with ethyl acetate. The fraction containing the product ($R_f$ 0.54, uniplate, ethyl acetate) was evaporated to give 3.35 g (98% yield) as an oil which was dissolved in 150 mL anhydrous diethyl ether and precipitated with 4.5N HCl in ethyl acetate, mp. 185°-188° C. Recrystallization of a small sample from methanol and diethyl ether did not change the melting point. IR 1650 cm$^{-1}$. $^1$H NMR (DMSO $d_6$) δ: 1.1 (d, 12H), 3.7 (s, 3H), 7.0 (m, 4H), $[\alpha]D^{25} = -11.67$, c 1.03 MeOH Elemental analysis for $C_{19}H_{31}N_3O_2 \cdot 2HCl$ Calc'd: C, 56.15; H, 8.18, N, 10.34; Cl, 17.45
Found: C, 55.76; H, 7.98; N, 9.98; Cl, 17.16;

EXAMPLE 8

N-2-(4-(2-Methoxyphenyl)-1-piperazine)ethyl 2,2-dimethylpropanamide

To a solution of 2-(4-(2-methoxyphenyl)-1-piperazine)ethyl amine (3.00 g, 0.0127 mol) in $CH_2Cl_2$ (80 mL) were added trimethylacetyl chloride (1.6 mL, 1.6 g, 0.013 mol) and triethylamine (2.0 mL, 2.8 g, 0.027 mol) successively. The solution was stirred at room temperature for 24 hours. The solution was washed with $H_2O$ and then brine and was dried with $MgSO_4$ and upon evaporation of $CH_2Cl_2$ gave 4.25 g of crude product. Purification by flash chromatography (silica gel, hexane, EtOAc, MeOH) provided a pure sample of the free base, 1.19 g. An additional 2.29 g of slightly impure product was recovered. Treatment of the pure sample in EtOH with HCl gave the dihydrochloride of the title compound, 1.13 g, mp. 243°-244° C.

Elemental analysis for $C_{18}H_{29}N_3O_2 \cdot 2HCl$

Calc'd: C, 55.10; H, 7.96; N, 10.71
Found: C, 54.78; H, 8.05; N, 10.56

EXAMPLE 9

N-(1,1-Dimethylethyl)-4-(2-methoxyphenyl)-1-piperazineacetamide

To a solution of t-butyl chloroacetamide (3.51 g, 0.0235 mol) in DMF (150–200 mL) was added successively 1-(2-methoxyphenyl)piperazine hydrochloride (5.35 g, 0.0234 mol) and triethyl amine (6.85 mL, 4.97 g, 0.0491 mol). The solution was stirred at 90° C. for 4 hours. The DMF was evaporated under reduced pressure. The residue was partitioned between $CH_2Cl_2$ and $H_2O$. The aqueous phase was extracted once with $CH_2Cl_2$. The combined organic phases were washed once with a small amount of $H_2O$ and dried with $MgSO_4$. Evaporation of the solvent gave the crude product (6.24 g) which was purified by flash chromatography (silica gel, EtOAc, hexane) to yield the free base (4.8 g). Treatment with HCl in EtOH gave the title compound as the dihydrochloride, mp. 105° C. (3.97 g, 43%).

Elemental analysis for $C_{17}H_{27}N_3O_2.2HCl.H_2O$

Calc'd: C, 51.51; H, 7.88; N, 10.670
Found: C, 51.59; H, 8.16; N, 10.39

EXAMPLE 10

N-(1,1-Dimethylethyl)-4-(2-pyrimidinyl)-1-piperazine-propanamide

To a suspension of t-butylamine hydrochloride (prepared by treatment of an $Et_2O$ solution of t-butylamine (2.7 mL, 1.9 g, 0.026 mol) with HCl) in a solution of 3-bromopropionic acid chloride (4.47 g, 0.0261 mol) with $CH_2Cl_2$ (145 mL) was added N,N-diisopropylethylamine (9.1 mL, 6.8 g, 0.052 mol) over 10–15 minutes at room temperature. The solution was stirred at room temperature for 2.5–3 hours. A few mL's of N,N-diisopropylethylamine were added until the solution became homogeneous. The solution was washed twice with dilute HCl and once with $H_2O$, dried with $MgSO_4$ and evaporated to provide 3.34 g of N-tert-butyl 3-bromopropanamide and N-tert-butyl acrylamide (approximately 36%/64% by weight). The reaction mixture was taken up in EtOH (200 mL), and to the solution of amides was added 1-(2-pyrimidinyl)piperazine dihydrochloride (6.82 g, 0.0288 mol) and sodium acetate (4.72 g, 0.0575 mol). The mixture was refluxed for 8 days. The solvent was evaporated. The residue was partitioned between $CH_2Cl_2$ and aqueous $Na_2CO_3$. The $CH_2Cl_2$ phase was washed with aqueous NaCl and dried with $MgSO_4$. Evaporation of the $CH_2Cl_2$ gave 5.61 of crude compound which was purified by HPLC to give 4.13 g of free base. Treatment in EtOH with HCl gave the title compound, 4.48 g (46%), mp 220°–222° C.

Elemental analysis for $C_{15}H_{25}N_5O.2HCl\frac{1}{2}H_2O$

Calc'd: C, 48.25; H, 7.55; N, 18.76
Found: C, 48.42; H, 7.45; N, 18.62

EXAMPLE 11

2,2-Dimethylpropanoic acid 2-[4-(2-pyrimidinyl)-1-piperazinyl]ethyl ester

Following the procedure of Example 3, with the exception that N-(2-pyrimidinyl)piperazine was substituted for N-(2-methoxyphenyl)piperazine, afforded the title compound which was converted to the dihydrochloride salt with ethereal HCl, mp. 185°–187° C.

Elemental analysis for $C_{15}H_{24}N_4O_2.2HCl$

Calc'd: C, 49.32; H, 7.12; N, 15.34
Found: C, 38.24; H, 3.69; N, 37.87

EXAMPLE 12

Tertiary-butyl 3-[1-[4-(2-methoxyphenyl)piperazinyl]]-2-phenyl-propanoate

A stirred suspension of 2-chloro-1-methylpyridinium iodide (3.28 g, 12.8 mmol) in toluene (20 mL) was treated under an atmosphere of nitrogen with atropic acid (1.80 g, 12.2 mol) treated with tert-butanol (0.92 mL, 11.8 mmol), treated with triethylamine (3.6 mL, 25.8 mmol), heated under reflux for 2 hours, cooled to room temperature and treated with water (100 mL) and diethyl ether (100 mL). The layers were separated and the aqueous layer extracted with diethyl ether (50 mL). The organic phases were combined, washed with water (100 mL), dried ($MgSO_4$), evaporated in vacuo, and the residue purified by chromatography [silica; hexane-ethyl acetate (20:1)] to give tert-butyl 2-phenylpropenoate (1.32 g) as an oil.

A solution of tert-butyl 2-phenylpropenoate (1.28 g, 6.3 mmol) and 1-(2-methoxyphenyl)piperazine (1.22 g; 6.4 mmol) in ethanol (10 mL) was maintained at room temperature for 3 days, evaporated in vacuo, and the yellow oil purified by chromatography [silic; hexane-ethyl acetate (5:1)] to give the free base of the product (1.96 g) as colorless crystals, mp. 99°–101° C.

A suspension of free base in hot methanol (20 mL) was acidified with ethereal hydrogen chloride. The resulting solution was cooled to cool temperature and the mixture evaporated in vacuo. The crystals were triturated with diethyl ether to give the dihydrochloride salt of the product (1.56 g), mp. 190°–193° C.

Elemental analysis for $C_{24}H_{32}N_2O_3.2HCl$

Calc'd: C, 61.4; H, 7.3; N, 6.0
Found: C, 61.3; H, 7.5; N, 6.0

EXAMPLE 13

N-Tertiary-butyl 3-[4-(2-methoxyphenyl)piperazinyl]-2-phenylpropanamide 1-(2-Methoxyphenyl)piperazine (22.6 g, 0.118 mol) and atropic acid (17.4 g, 0.118 mol) in ethanol (300 mL) were heated under reflux for 18 hours, cooled to room temperature, and evaporated in vacuo. The solid was triturated with acetone (3×100 mL) to give a first crop of 3-[4-(2-methoxyphenyl)piperazinyl]-2-phenylpropionic acid (13.8 g) as white crystals. The filtrate was evaporated in vacuo to give an oil which slowly crystallized over 1 month. The solid was triturated with acetone (200 mL) to give a second crop of the same hemihydrate product (9.01 g) as white crystals, mp. 160°–163° C.

Elemental analysis for $C_{20}H_{24}N_2O_3.\frac{1}{2}H_2O$

Calc'd: C, 68.8; H, 7.2; N, 8.0
Found: C, 68.4; H, 7.2; N, 7.9

A stirred suspension of 3-[4-(2-methoxyphenyl)-piperazinyl]-2-phenylpropionic acid (5.05 g; 14.7 mmol) in dichloromethane (30 ml) was treated with 1,1-carbonyldiimidazole (2.67 g, 16.5 mmol) and, after 35 minutes, the resulting solution was treated with tert-butylamine (1.9 ml, 18.2 mmol). After 18 hours, the mixture was evaporated in vacuo and the residue purified by chromatography (silica, diethyl ether) to give the product (2.80 g, 48%) as white crystals. A suspension of the solid in methanol-isopropanol (2 ml+6 ml) was acidified with ethereal hydrogen chloride to give a solution which was evaporated in vacuo to give a solid. Trituration with diethyl ether gave the dihydrochloride salt of the product (3.30 g), mp. 230°–231° C.

Elemental analysis for $C_{24}H_{33}N_3O_2.2HCl$

Calc'd: C, 61.5; H, 7.5; N, 9.0
Found: C, 61.4; H, 7.5; N, 8.9

EXAMPLE 14

N-Tertiary-butyl 2-[[4-(2-methoxyphenyl)piperazinyl]methyl]-3-phenyl-propanamide 2-(Phenylmethyl)propenoic acid (Mannich et al., Chem. Ber., 1922, 55, 3486) (2.00 g, 12.35 mmol) and 1-(2-methoxyphenyl)piperazine (2.37 g, 12.35 mmol) in propanol (25 mL) were boiled under reflux for 18 hours, cooled to room temperature, and evaporated in vacuo. The residue was triturated with acetone and diethyl ether to give 2-[[4-(2-methoxyphenyl)piperazinyl]methyl]-3-phenyl propanoic acid (0.80 g) as a colorless powder, mp. 155°–158° C.

Elemental analysis for $C_{21}H_{26}N_2O_3$

Calc'd: C, 71.2; H, 7.3; N, 7.9
Found: C, 71.6; H, 7.4; N, 7.6

The product of the preceding paragraph (1.60 g, 4.5 mmol) in dichloromethane was treated with 1,1'-carbonyldiimidazole (0.73 g, 4.5 mmol), stirred for one hour, treated in tertiary butylamine (0.66 g, 9.0 mmol), stirred for eighteen hours, evaporated in vacuo and the residue was chromatographically purified (silica; diisopropyl ether gradient to diethyl ether). The product was dissolved in hot isopropanol and treated with ethereal HCl to obtain the title compound as the hydrochloride salt (0.43 g), mp. 127.5°–130° C.

Elemental analysis for $C_{25}H_{35}N_3O_2.HCl.\frac{1}{4}H_2O$

Calc'd: C, 65.4; H, 8.2; N, 9.2
Found: C, 65.1; H, 8.0; N, 8.9

EXAMPLE 15

N-[2-[4-(2-Methoxyphenyl)-1-piperazinyl)ethyl]-1-methylcyclohexanecarboxamide

To a solution of 2-(4-(2-methoxyphenyl)-1-piperazinyl)ethyl amine (1.49 g, 0.00633 mol) in $CH_2Cl_2$ (40 mL), 1-methylcyclohexylcarboxylic acid chloride (1.00 g, 0.00622 mol) and triethylamine (1.0 mL, 0.73 g, 0.0072 mol) were added and the mixture stirred at room temperature overnight. The solution was washed with water and dried with $MgSO_4$. Evaporation gave 2.28 g of crude material which was purified by HPLC to give the pure free base, 1.54 g. Treatment with HCl in EtOH gave the title compound as the dihydrochloride, 1.36 g (51%), mp. 180°–197° C.

Elemental analysis for $C_{21}H_{33}N_3O_2.2HCl.\frac{1}{4}H_2O$

Calc'd: C, 57.13; H, 8.22; N, 9.52
Found: C, 57.40; H, 7.93; N, 9.39

EXAMPLE 16

4-(2-Methoxyphenyl)-N-(1-methylcyclohexyl)-1-piperazinepropanamide

To a suspension of 1-methyl-cyclohexylamine hydrochloride (4.59 g, 0.0307 mol) in $CH_2Cl_2$ (150 mL) was added 3-bromopropionyl chloride (5.26 g, 0.0307 mol). Diisopropyl ethyl amine (20.7 mL, 15.4 g, 0.119 mol) was added slowly. The mixture was stirred at room temperature overnight. The organic phase was filtered, washed and aqueous HCl, water, and dried with $MGSO_4$. Evaporation of the $CH_2Cl_2$ gave 5.03 g of a mixture of N-1-methylcyclohexyl-2-bromopropanamide and N-1-methylcyclohexyl acrylamide in a ratio of 1 to 3. This mixture (3.0 g, 0.016 mol) was taken up in EtOH (142 mL). To this solution was added 1-(2-methoxyphenyl)piperazine hydrochloride (4.34 g, 0.0190 mol) and sodium acetate (1.58 g, 0.0193 mol). The mixture was refluxed two days. The EtOH was evaporated. The residue was partitioned between $H_2O$ and $CH_2Cl_2$. The $CH_2Cl_2$ phase dried with $MgSO_4$. Evaporation of $CH_2Cl_2$ gave crude product, 6.77 g. Purification by HPLC gave the pure free base, 2.38 g, which was treated with HCl in EtOH to give the title compound as the dihydrochloride, 2.53 g (37%, based on the amide mixture), mp. 198°–203° C.

Elemental analysis for $C_{21}H_{33}N_3O_2.2HCl$

Calc'd: C, 58.33; H, 8.16; N, 9.72
Found: C, 58.00; H, 8.39, N, 9.63

EXAMPLE 17

4-(2-Pyrimidinyl)-N-(1-methylcyclohexyl)-1-piperazinepropanamide

The title compound was prepared from -1-(2-pyrimidyl)piperazine dihydrochloride (2.77 g, 0.0117 mol), sodium acetate (1.92 g, 0.0234 mol) and the mixture of 3-N-1-methylcyclohexyl-bromopropanamide and N-1-methylcyclohexyl acrylamide (1.8 g, 0.0098 mol) in the manner described in Example 16 to give 1.36 g of the title compound as the dihydrochloride (32%, based on the amide mixture), mp. 204°–209° C.

Elemental analysis for $C_{18}H_{29}N_5O.2HCl.3/2H_2O$

Calc'd: C, 50.1; H, 7.94; N, 16.24
Found: C, 49.84; H, 7.97; N, 16.19

EXAMPLE 18

N-[2-[4-(2-Methoxyphenyl)-1-piperazinyl]ethyl]-N'-(1-methylcyclohexyl)urea

To a solution of oxalyl chloride (35 mL, 51 g, 0.40 mol) in $CH_2Cl_2$ (214 mL) at room temperature was added solid 1-methyl-1-cyclohexanecarboxylic acid (20.05 g, 0.1410 mol). The solution was stirred at room temperature overnight. The solvent and excess oxalyl chloride were evaporated. The residue was stripped with $CH_2Cl_2$ twice. The 1-methyl-1-cyclohexanecarboxylic acid chloride (20.00 g, 0.1425 mol) in $Et_2O$, (110 mL) was added to a stirred suspension of concentrated aqueous $NH_3$ (31 mL) in $Et_2O$ 300 mL at room temperature. The mixture was stirred at room temperature for 3–4 hours. The aqueous layer was acidified to pH 1–2 with 6M HCl and brine was added. The $Et_2O$ layer was separated and washed once with aqueous NaCl, dried with $MgSO_4$ and evaporated to remove the $Et_2O$ to give 16.40 g of the desired carboxamide. To a solution of $Br_2$ (3.7 mL, 11 g, 0.072 mol) in 20% KOH in $H_2O$ (197 mL) at 0° C. was added solid 1-methyl-1-cyclohexanecarboxamide (10.00 g, 0.07082 mol). The solution was stirred for 2–3 hours at 0° C. and then extracted with $Et_2O$ twice. Drying with $MgSO_4$ and evaporation of the $Et_2O$ gave 1-methyl-1-cyclohexylisocyanate (5.84 g) as an oil which crystallized slowly.

To a solution of 2-(4-(2-methoxyphenyl)-1-piperazinyl)ethyl amine (2.02 g, 0.00858 mol) in CH$_2$Cl$_2$ (50 mL) was added 1-methylcyclohexyl isocyanate (1.20 g, 0.00862 mol) and the mixture was stirred at room temperature overnight. The mixture was washed once with H$_2$O, dried with MgSO$_4$ and evaporated to give the crude product (3.53 g) which was purified by HPLC to give the free base, (2.04 g). Treatment with HCl in EtOH gave the title compound as the dihydrochloride (1.06 g, 26%), mp. 155°–161° C.

Elemental analysis for C$_{21}$H$_{34}$N$_4$O$_2$.2HCl.3/2H2O

Calc'd: C, 53.16; H, 8.29; N, 11.81
Found: C, 53.26; H, 8.24; N, 11.75

EXAMPLE 19

N-2-(4-(2-Pyrimidinyl)-1-piperazinyl)ethyl-1-methylcyclohexylcarboxamide

The title compound was prepared from 2-(4-(2-pyrimidinyl)-1-piperazinyl)ethyl amine (1.50 g, 0.00724 mol), 1-methylcyclohexylcarboxylic acid chloride (1.16 g, 0.00722 mol) and triethylamine (1.1 mL, 0.80 g, 0.0079 mol) in the manner previously described to give 1.80 g (62%) of product, mp. 212°–220° C.

Elemental analysis for C$_{18}$H$_{29}$N$_5$O.2HCl

Calc'd: C, 53.47; H, 7.73; N, 17.32
Found: C, 53.1; H, 7.77; N, 17.15

EXAMPLE 20

(R)-N-[2-[4-(2-Methoxyphenyl)-1-piperazinyl]-1-methylethyl]-1-methylcyclohexane carboxamide To a chilled solution of t-butoxycarbonyl D-alanine (9.45 g, 0.05 mol) and 1-(2-methoxyphenyl)piperazine (9.6 g, 0.05 mol) in 125 mL of CH$_2$Cl$_2$ was added diethyl cyanophosphonate (8.34 mL, 0.055 mol) in 50 mL of CH$_2$Cl$_2$ over 30 minutes followed by triethylamine (7.37 mL, 0.055 mol) in 50 mL of CH$_2$Cl$_2$ over 15 minutes. After 2½ hours, the solution was washed with water (2×100 mL) and K$_2$CO$_3$ (2×100 mL of 10% aqueous), dried over anhydrous K$_2$CO$_3$ and evaporated to an oil. The crude 1-(t-butoxycarbonyl-D-alanyl)-4-(2-methoxyphenyl)piperazine was stirred in 200 mL of 4.5N HCl in ethyl acetate for 1 hour at room temperature, diluted with 400 mL of anhydrous diethyl ether, filtered, washed and dried in vacuo. The 1-(D-alanyl)-4-(2-methoxyphenyl)piperazine dihydrochloride was stirred in 200 mL of anhydrous tetrahydrofuran, treated with 225 mL of 1M BH$_3$ in tetrahydrofuran, and refluxed 3½ hours. After cooling in ice, the reaction was quenched with 140 mL of 2N aqueous HCl and refluxed 18 hours. The tetrahydrofuran was removed on a Rotovapor, the aqueous solution was made basic with 6N sodium hydroxide and the amine was extracted into diethyl ether. The diethyl ether solution was dried over anhydrous K$_2$CO$_3$, filtered and acidified with 4.5N HCl in ethyl acetate. The salt was filtered, washed with diethyl ether, converted to free base in 2N NaOH and extracted into diethyl ether. After drying as above and evaporation, (R)-1-methyl-2-[4-(2-methoxyphenyl)-piperazinyl]ethylamine was obtained as an oil (11.8 g, 94.7% based on BOC-D-alanine). A sample was converted to the trihydrochloride sesquihydrate, mp. 219°–221° C.; [α]D$^{25}$=−26.4 c=0.99 MeOH. 1H NMR (DMSO-d$_6$) δ: 1.32 (d, 3H), 3.8 (s, 3H), 6.9–7.0 (m, 4H). The IR curve was devoid of carbonyl peaks.

Elemental analysis for C$_{14}$H$_{23}$N$_3$O.3HCl.1.5H2O

Calc'd: C, 43.59; H, 7.58; N, 10.89
Found: C, 43.47; H, 7.08; N, 10.57

(R)-[1-Methyl-2-[4-(2-methoxyphenyl)-1-piperazinyl]ethylamine (2.49 g, 0.01 mol) and 1-methylcyclohexane carboxylic acid (2.84 g, 0.02 mol) in 25 mL of CH$_2$Cl$_2$ were chilled in ice and treated with diethylcyanophosphonate (3.26 g, 3.1 mL, 0.02 mol) in 10 mL of CH$_2$Cl$_2$ over 15 minutes followed by N-methyl morpholine (2.02 g, 2.2 mL, 0.02 mol) in 10 mL of CH$_2$Cl$_2$ over 15 minutes. After stirring overnight, the solution was washed with 2N NaOH (2×50 mL), water (2×50 mL) and dried (anhydrous K$_2$CO$_3$). The product was isolated using dry column chromatography on silica gel (300 g) and development with ethyl acetate. The product (Rf 0.59 uniplate, ethyl acetate) was dissolved in 150 mL of diethyl ether and precipitated with 4.5N HCl in ethyl acetate. Recrystallization from methanol/diethyl ether gave the pure title compound as the dihydrochloride, mp. 180°–185° C., [α]$^{25}$−9.32 c=1.09 MeOH.

Elemental analysis for C$_{22}$H$_{35}$N$_3$O$_2$.2HCl

Calc'd: C, 59.18; H, 8.35; N, 9.41
Found: C, 58.90; H, 8.21; N, 9.04

EXAMPLE 21

(R)-1-Methyl-N-[1-methyl-2-[4-(2-pyrimidinyl)]-1-piperazinyl]ethyl]cyclohexane carboxamide In a manner analagous to Example 20 using t-butoxycarbonyl-D-alanine and 1-benzylpiperazine, (R)-1-methyl-2-[4-phenylmethyl-1-piperazinyl]ethyl amine was obtained as an oil. A sample was converted to the trihydrochloride, dihydrate, mp. 246°–248° C.

Elemental analysis for C$_{14}$H$_{23}$N$_3$.3HCl.2H2O

Calc'd: C, 44.39; H, 7.92; N, 11.09
Found: C, 44.43; H, 6.89; N, 10.71

In a manner analagous to Example 20 using (R)-1-methyl-2-[4-phenylmethyl-1-piperazinyl]ethylamine and 1-methylcyclohexanecarboxylic acid, (R)-1-methyl-N-[1-methyl-2-[[(4-phenylmethyl-1-piperazinyl)ethyl]cyclohexanecarboxamide was obtained after crystallization from methanol and diethyl ether, mp. 168°–170° C., [α]$^{25}$−8.85 c=1.02 MeOH.

Elemental analysis for C$_{22}$H$_{35}$N$_3$O.2HCl.1½H2O

Calc'd: C, 57.75; H, 8.81; N, 9.18
Found: C, 57.73; H, 8.76; N, 9.19

The product from the preceding paragraph (6.91 g, 0.0151 mol) and 10% palladium on carbon (1 g) were shaken in 95% ethanol (200 mL) on a Parr hydrogenation apparatus until hydrogen uptake stopped and TLC on a sample of base showed no starting material (20 hours). The catalyst was removed by filtration and the filtrate was evaporated to dryness. The solid together with 2-chloropyrimidine (1.81 g, 0.0158 mol), powdered anhydrous potassium carbonate (20.7 g, 0.15 mol) and triethylamine (1 mL) were stirred at 65°–70° C. in dimethylformamide (100 mL) overnight. The solvent was removed on a Rotovapor and the residue was partitioned between water and dichloromethane. The organic layer was washed with water, dried over sodium sulfate and evaporated. The title compound crystallized from hexane. Yield 2.58 g 49.4%, mp. 96°–98° C., [α]$^{25}$−22.9 c=1.00 MeOH.

Elemental analysis for $C_{19}H_{31}N_5O$

Calc'd: C, 66.05; H, 9.04; N, 20.2
Found: C, 65.86; H, 9.43; N, 19.92

EXAMPLE 22

N-(1,1-Dimethylethyl)-4-(2-methoxyphenyl)-piperazinylpropanamide

A solution of N-tert-butylacrylamide (1.799 g, 14.2 mmol) and 1-(2-methoxyphenyl)piperazine (2.111 g, 11.0 mmol) in propanol (20 mL) was maintained at room temperature for 8 days, evaporated in vacuo, and chromatographed [silica; ethanol-ethyl acetate (1:20)] to give the free base of the product as a yellow oil (2.52 g, 72%).

The oil was dissolved in propan-2-ol (10 mL) and the solution acidified with ethereal hydrogen chloride. The mixture was evaporated in vacuo and the precipitate washed with diethyl ether to give the product as the dihydrochloride quarter hydrate (2.36 g, mp. 245°–248° C. (dec).

Elemental analysis for $C_{18}H_{29}N_3O_2.2HCl.\frac{1}{4}H_2O$

Calc'd: C, 54.5; H, 8.0; N, 10.6
Found: C, 54.9; H, 8.1; N, 10.5

EXAMPLE 23

2,2-Dimethylpropanoic acid 2-(4-(2-methoxyphenyl)-piperazin-1-yl)-1-phenylethyl ester A solution of 2,2-dimethylpropanoic acid chloride (0.28 g, 2.34 mmoles) in dichloromethane (10 mL) was added dropwise to a stirred solution of 2-(4-(2-methoxyphenyl)piperazin-1-yl)-1-phenylethanol dihydrochloride (0.90 g, 2.34 mmoles) and triethylamine (0.73 g, 7.2 mmoles) in dichloromethane (15.0 mL). The reaction mixture was stirred at room temperature over the weekend and a further quantity of the same acid chloride (0.14 g, 1.17 mmoles) and triethylamine (0.30 g, 1.17 mmoles) was added. The reaction mixture was stirred overnight, filtered, concentrated under reduced pressure and chromatographed on silica gel. Elution with hexane:ethyl acetate (2:1) afforded an oil which was dissolved in acetonitrile and acidified with ethereal hydrogen chloride to give colourless crystals of the title compound as the dihydrochloride (0.91 g), mp. 237.9°–240.9° C. (dec).

Elemental analysis for $C_{24}H_{32}N_2O_3.2HCl$

Calc'd: C, 61.4; H, 7.3; N, 6.0
Found: C, 61.1; H, 7.4; N, 6.3

EXAMPLE 24

O-(2-(4-(2-Methoxyphenyl)piperazin-1-yl)ethyl)-N-(2-methyl-2-propyl)carbamate

Tributyltin methoxide (0.05 ml, 0.20 mmoles) was added to a solution of 2-(4-(2-methoxyphenyl)piperazin-1-yl)-1-phenyl-ethanol (1.50 g, 4.8 mmoles) and t-butyl isocyanate (0.52 g, 5.3 mmoles) in toluene (15.0 mL). The reaction mixture was stirred for two days at room temperature and then chromatographed on silica gel, gradient eluting with hexane:ethyl acetate (2:1 to 1:2) to afford a colourless low-melting solid (1.93 g) which solidified on standing. The crude product was dissolved in ethyl acetate and acidified with ethereal hydrogen chloride to afford a colourless powder of the title compound as the dihydrochloride (1.63 g), mp. 184.3°–188.3° C.

Elemental analysis for $C_{24}H_{33}N_3O_3.2HCl$

Calc'd: C, 59.4; H, 7.5; N, 8.7
Found: C, 59.8; H, 7.5; N, 8.7

EXAMPLE 25

N-Tert-butyl-2-methoxyphenyl-3-(4-(2-methoxyphenyl)-piperazin-1-yl)propanamide

A solution of potassium tert-butoxide (5.15 g, 46.0 mmols) in warm tert-butanol (21 ml) was added to a cooled (ice-methanol) suspension of 1-(2-[2-methoxyphenyl]-2-oxo)ethyl-4-(2-methoxyphenyl)piperazine dihydrochloride (5.00 gm, 12.11 mmols) and tosylmethylisocyanide (2.60 g, 13.31 mmols) in dry dimethoxyethane (100 mL). The reaction mixture was slowly allowed to warm to room temperature over 2 hours. Acetic acid (0.80 g, 13.33 mmols) was added to the reaction mixture followed by the addition of ethyl acetate (200 mL). The precipitate formed was filtered off and the filtrate concentrated to about 50 mL under reduced pressure. The concentrate was dissolved in water and washed with ethyl acetate. The combined organic phases were washed with brine, water, dried (MgSO$_4$) and concentrated to afford a brown oil. The crude product was chromatographed on silica gel and gradient eluted with hexane:ethyl acetate (3:2) to ethyl acetate, to afford a brown oil (3.30 g). A sample (1.0 g) of the oil was dissolved in diisopropylether and acidified with ethereal hydrogen chloride to afford off-white crystals which were recrystallized from diethyl-ether in methanol to give 2-(2-methoxyphenyl)-3-(4-(2-methoxyphenyl)-piperazin-1-yl)propanenitrile as a dihydrochloride quarterhydrate as colourless crystals (0.75 g), mp. 189°–192° C.

Elemental analysis for $C_{21}H_{25}N_3O_2.2HCl.\frac{1}{4}H_2O$

Calc'd: C, 58.9; H, 6.5; N, 9.8
Found: C, 58.7; H, 6.5; N, 9.5

Tert-butanol (1.20 g, 16.2 mmoles) was added to an ice-cooled solution of 2-(2-methoxyphenyl)-3-(4-(2-methoxyphenyl)piperazin-1yl)propanonitrile dihydrochloride (1.90 g, 5.41 mmoles) in methane-sulphonic acid (10.0 mL) and the reaction mixture stirred at room temperature for 48 hours. The reaction mixture was poured onto ice and basified with a mixture of 2M sodium hydroxide and solid sodium hydroxide. The aqueous layer was washed with ethyl acetate (3×30 mL) and the combined organic phases washed with brine (30 mL), water (30 mL), dried (MgSO$_4$) and concentrated to afford a brown oil. The crude product was chromatographed on silica gel and gradient eluted with ethyl acetate:hexane (1:1 to 4:1) and finally ethyl acetate to give a brown oil (2.06 g) which solidified on standing. The crude product was dissolved in diethyl ether and acidified with ethereal hydrogen chloride to afford a powder which was triturated in diisopropylether and then recrystallised from a mixture of diisopropylether and ethanol to afford the title compound as a dihydrochloride hydrate (0.30 g), mp. 129.0°–132.5° C.

Elemental analysis for $C_{25}H_{35}N_3O_3.2HCl.H_2O$

Calc'd: C, 58.1; H, 7.6; N, 8.1
Found: C, 58.5; H, 7.9; N, 7.7

EXAMPLE 26

N-Tert-butyl-3-[1-[4-(2-methoxy)phenyl]piperazinyl]-2-phenyl-propionhydrazide

A suspension of tert-butylhydrazine hydrochloride (0.63 g, 5.0 mmol) in dry tetrahydrofuran (20 mL) was treated with triethylamine (0.7 mL, 0.5 g, 5.0 mmol). To the suspension were added 3-[1-[4-(2-methoxy)phenyl]-piperazinyl]-2-phenylpropionic acid (1.70 g, 5.0 mmol) and N,N-dicyclohexylcarbodiimide (1.03 g, 5.0 mmol) and the mixture was stirred at room temperature for 18 hours. The mixture was concentrated in vacuo and the residue was extracted with hot ethyl acetate (50 mL). The precipitate was filtered off and washed, and the filtrate was concentrated in vacuo. The product was chromatographed on silica with eluant ethyl acetate:toluene, 1:4/ethyl acetate to give the title compound as the free base (0.79 g), which was dissolved in ethyl acetate (40 mL) to give a solution. This was acidified with ethereal hydrogen chloride (5 mL) to give a precipitate which was triturated with acetonitrile to give the title compound as the dihydrochloride trihydrate (0.56 g), mp. 208°–210° C.

Elemental analysis for $C_{24}H_{34}N_4O_2.2HCl.3H_2O$

Calc'd: C, 53.6; H, 7.9; N, 10.49
Found: C, 53.7; H, 7.6; N, 10.2

EXAMPLE 27

O-Tert-butyl-3-[1-(4-(2-methoxy)phenyl)piperazinyl)-2-phenyl-propionohydroxamate A stirred suspension of O-tert-butylhydroxylamine hydrochloride (628 mg, 5.0 mmol) in dry tetrahydrofuran (20 mL) was treated successively with triethylamine (1.4 mL, 1.02 g, 10 mmol), and 3-[1-[4-(2-methoxy)-phenyl]piperazinyl]-2-phenylpropionic acid (1.70 g, 5.0 mmol). A solution of dicyclohexylcarbodiimide (1.03 g, 5.0 mmol) in dry tetrahydrofuran (5 mL) was added, and the mixture was stirred for 2 hours and was allowed to stand for 81 hours. The suspension was concentrated in vacuo and extracted with hot ethyl acetate (2×40 mL). The extracts were concentrated in vacuo and the residue chromatographed on silica with eluant ethyl acetate:toluene 1:4/ethyl acetate to give the title compound as the free base (1.39 g). The product was dissolved in methanol (70 mL), and the solution was acidified with ethereal hydrogen chloride (5 mL), concentrated in vacuo and the product triturated with acetonitrile to give the title compound as the dihydrochloride (512 mg), mp. 188° C. (dec).

Elemental analysis for $C_{24}H_{33}N_3O_3.2HCl.2H_2O$

Calc'd: C, 57.4; H, 7.4; N, 8.4
Found: C, 57.6; H, 7.4; N, 8.35

The compounds of this invention have been demonstrated to possess $5HT_{1A}$ receptor binding properties which characterize them as useful anxiolytic and/or antidepressant agents. Where the compounds of this invention also display $D_2$ receptor site binding properties, they also have an anti-psychotic element which is of use in treatment of anxiety, depression, senile dementia (SDAT), Huntington's chorea, stroke and sexual disturbances.

Those compounds in which $R^5$ is alkyl of 4 to 8 carbon atoms or optionally substituted phenyl or benzyl, selectively bind to receptors of the $5-HT_{1A}$ type to a much greater extent than they bind to other receptors such as $a_1$ and $D_2$ receptors.

The pharmacological profile of the compounds of this invention resembles that of buspirone obtained by measuring the compound's ability to displace [$^3$H] 8-OH DPAT (dipropylaminotetralin) from the $5-HT_{1A}$ serotonin receptor by the procedure of Hall et al., J. Neurochem. 44: 1685–1696, 1985. The compounds of this invention, like buspirone, exhibited potent affinity for this serotonin receptor subtype. The anxiolytic activity of buspirone is currently believed to be due, at least in part, to this receptor (Vander Maclen et al., Eur. J. Pharmacol. 1986, 129 (1-2) 123–130.

The $D_2$ dopamine receptor binding study was in accordance with a modification of the procedure of Field et al., Brain Res., 136, pp. 578–584 (1977) and Yamamura et al., eds., Neurotransmitter Receptor Binding, Raven Press, N.Y. (1978), wherein homogenized limbic brain tissue is incubated with $^3$H-spiroperidol and various concentrations of test compounds, filtered and washed and shaken with Hydrofluoro scintillation cocktail (National Diagnostics) and counted in a Packard 460CD scintillation counter. The test results of these studies are as follows:

| Compound of | Affinity for $5HT_{1A}$ Receptor % Inhibition | Affinity for $D_2$ Receptor % Inhibition |
|---|---|---|
| Example 1 | 91 at 0.1 μM | |
| Example 2 | 100 at 0.1 μM | |
| Example 3 | 86 at 1 μM | 89 at 1 μM |
| Example 4 | 98 at 1 μM | 99 at 1 μM |
| Example 5 | 98 at 1 μM | 58 at 1 μM |
| Example 12 | $IC_{50}$ 11.8 nM | |
| | 98 at 1 μM | |
| | 86 at 0.1 μM | |
| Example 13 | $IC_{50}$ 25.0 nM | $IC_{50}$ 1740 nM |
| | 86 at 1 μM | 32 at 1 μM |
| | 69 at 0.1 μM | 8 at 0.1 μM |
| Example 14 | $IC_{50}$ 11.4 nM | 38 at 10 μM |
| | 100 at 1 μM | |
| | 90 at 0.1 μM | |
| Example 15 | 98 at 0.1 μM | |
| Example 16 | 56 at 0.1 μM | |
| Example 18 | 85 at 0.1 μM | |
| Example 19 | 67 at 0.1 μM | |
| Example 20 | 100 at 0.1 μM | |
| Example 22 | $IC_{50}$ 287.0 nM | |
| | 72 at 1 μM | |
| | 18 at 0.1 μM | |
| Example 23 | $IC_{50}$ 270.0 nM | |
| | 78 at 1 μM | |
| | 27 at 0.1 μM | |
| Example 24 | $IC_{50}$ 20.0 nM | |
| | 97 at 1 μM | |
| | 73 at 0.1 μM | |
| Example 26 | $IC_{50}$ 118.0 nM | |
| | 96 at 1 μM | |
| | 48 at 0.1 μM | |

The very weak $D_2$ receptor binding exhibited by the compounds of Examples 13 and 14 illustrate the selective $5HT_{1A}$ receptor binding properties of those compounds mentioned, supra, where $R^5$ is alkyl of 4 to 8 carbon atoms or an optionally substituted phenyl or benzyl moiety.

Hence, the compounds of this invention are anxiolytic and/or antidepressant agents useful in the treatment of depression and in alleviating anxiety and in those instances where meaningful $D_2$ binding occurs as antipsychotic agents for treatment of psychoses such as paranoia and schizophrenia, as well as the related secondary conditions of sexual dysfunction, senile dementia (SDAT) and the like. As such, the compounds may be administered neat or with a pharmaceutical carrier to a patient in need thereof. The pharmaceutical carrier may be solid or liquid.

A solid carrier can include one or more substances which may also act as flavoring agents, lubricants, solubilizers, suspending agents, filters, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain suitable pharmaceutical additives such as solubilizers, emulsifiers, buffers, preservatives, sweeteners, flavoring agents, suspending agents, thickening agents, colors, viscosity regulators, stabilizers or osmoregulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellents.

Liquid pharmaceutical compositions which are sterile solutions or suspensions can be utilized by, for example, intramuscular, intraperitoneal or subcutaneous injection. Sterile solutions can also be administered intravenously. When the compound is orally active, it can be administered orally either in liquid or solid composition form.

Preferably, the pharmaceutical composition is in unit dosage form, e.g., as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis of state of anxiety and the size, age and response of the patient.

What is claimed is:

1. A compound of the formula:

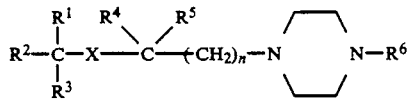

in which
$R^1$ is alkyl of 1 to 6 carbon atoms;
$R^2$ and $R^3$ are alkyl of 1 to 6 carbon atoms or taken together they are polymethylene of 2 to 12 carbon atoms or taken together with the carbon atom to which they are attached, $R^2$ and $R^3$ complete a 5-norbornen-2-yl moiety;
X is —$CO_2$—, —OCO—, —$OCO_2$—, —$N(R^7)CO$—, —NHNHCO—, —$ON(R^7)CO$—, —$CON(R^7)$—, —$N(R^7)CO_2$—, —$OCON(R^7)$— or —$N(R^7)CON(R^8)$—; wherein $R^7$ and $R^8$ are, independently, hydrogen, alkyl of 1 to 6 carbon atoms, phenyl, benzyl, substituted phenyl or substituted benzyl in which the substituents are halo, alkyl of 1 to 6 carbon atoms, alkoxy of 1 to 6 carbon atoms, cyano, nitro or perhalomethyl;
$R^4$ is hydrogen or alkyl of 1 to 6 carbon atoms;
$R^5$ is hydrogen, alkyl of 1 to 8 carbon atoms, hydroxyalkyl of 1 to 3 carbon atoms, phenyl, benzyl, substituted phenyl or substituted benzyl in which the substituents are hydroxy, halo, alkyl of 1 to 6 carbon atoms, alkoxy of 1 to 6 carbon atoms, trifluoromethyl, nitro, cyano, carbalkoxy of 2 to 7 carbon atoms, carboxamide, amino, alkylamino of 1 to 6 carbon atoms or dialkylamino of 2 to 12 carbon atoms;
$R^6$ is phenyl, benzyl, 2-, 3-, or 4-pyridinyl, 2-pyrimidinyl or 2-pyrazinyl; any of which may be substituted by one or more hydroxy, halo, alkyl of 1 to 6 carbon atoms, alkoxy of 1 to 6 carbon atoms, trifluoromethyl, nitro, cyano, carbalkoxy of 2 to 7 carbon atoms, carboxamido, amino, alkylamino of 1 to 6 carbon atoms or dialkylamino of 2 to 12 carbon atoms;
and
n is one of the integers 0, 1, 2, 3, 4 or 5; or a pharmaceutically acceptable salt thereof, with the proviso that when X is —$CON(R^7)$— and $R^7$ is alkyl, $R^6$ is other than 2-pyrimidinyl and when X is —$CO_2$— and $R^1$, $R^2$ and $R^3$ are methyl and n is 1, $R^6$ is other than 3,5-di(trifluoromethyl)phenyl.

2. A compound of claim 1 of the formula:

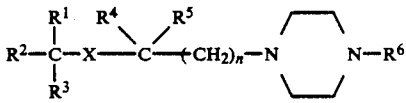

in which
$R^1$ is alkyl of 1 to 6 carbon atoms;
$R^2$ and $R^3$ are alkyl of 1 to 6 carbon atoms or taken together they are polymethylene of 2 to 6 carbon atoms or taken together with the carbon atom to which they are attached, $R^2$ and $R^3$ complete a 5-norbornen-2-yl moiety;
X is —$CO_2$—, —OCO—, —$OCO_2$—, —$N(R^7)CO$—, —NHNHCO—, —$ON(R^7)CO$—, —$CON(R^7)$—, —$N(R^7)CO_2$—, —$OCON(R^7)$— or —$N(R^7)CON(R^8)$—; wherein $R^7$ and $R^8$ are, independently, hydrogen, alkyl of 1 to 6 carbon atoms, phenyl, benzyl, substituted phenyl or substituted benzyl in which the substitutents are halo, alkyl of 1 to 6 carbon atoms, alkoxy of 1 to 6 carbon atoms, cyano, nitro or perhalomethyl;

R⁴ is hydrogen or alkyl of 1 to 6 carbon atoms;

R⁵ is hydrogen, alkyl of 1 to 6 carbon atoms, hydroxyalkyl of 1 to 3 carbon atoms, phenyl, benzyl, p-hydroxyphenyl, p-methoxyphenyl, o-methoxyphenyl, p-chlorophenyl or p-fluorophenyl;

R⁶ is phenyl, 2-alkylphenyl in which the alkyl substituent has 1 to 6 carbon atoms, 2-alkoxyphenyl in which the alkoxy substituent has 1 to 6 carbon atoms, 2-halophenyl, 2-cyanophenyl, 2-nitrophenyl, 2-perhalomethylphenyl, benzyl, 2-, 3-, or 4-pyridinyl, 2-pyrimidinyl or 2-pyrazinyl;

and n is one of the integers 0, 1, 2, 3, 4 or 5; or a pharmaceutically acceptable salt thereof, with the proviso that when X is —CON(R⁷)— and R⁷ is alkyl, R⁶ is other than 2-pyrimidinyl.

3. A compound of claim 1 in which R² and R³ are, independently, alkyl of 1 to 6 carbon atoms.

4. A compound of claim 2 in which R⁴ is hydrogen and R⁵ is alkyl of 1 to 6 carbon atoms, phenyl or benzyl.

5. A compound of claim 2 in which R⁶ is 2-methoxyphenyl, 2-chlorophenyl or 2-pyrimidinyl.

6. A compound of the formula:

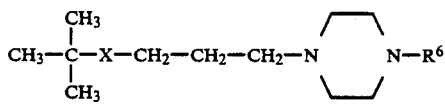

in which

X is —CO₂— or —NHCO₂—;

R⁶ is 2-, 3- or 4-pyridinyl, 2-pyrimidinyl or 2-pyrazinyl, or a pharmaceutically acceptable salt thereof.

7. A compound of the formula:

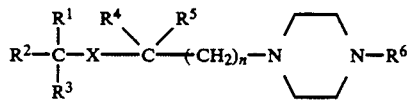

in which

R¹ is alkyl of 1 to 6 carbon atoms;

R² and R³, taken together, are polymethylene of 2 to 12 carbon atoms or taken together with the carbon atom to which they are attached, R² and R³ complete a 5-norbornen-2-yl moiety;

X is —CO₂—, —OCO—, —OCO₂—, —N(R⁷)CO—, —NHNHCO—, —ON(R⁷)CO—, —CON(R⁷)—, —N(R⁷)CO₂—, —OCON(R⁷)— or —N(R⁷)CON(R⁸)—, wherein R⁷ and R⁸ are, independently, hydrogen, alkyl of 1 to 6 carbon atoms, phenyl, benzyl, substituted phenyl or substituted benzyl in which the substituents are halo, alkyl of 1 to 6 carbon atoms, alkoxy of 1 to 6 carbon atoms, cyano, nitro or perhalomethyl;

R⁴ is hydrogen or alkyl of 1 to 6 carbon atoms;

R⁵ is hydrogen, alkyl of 1 to 8 carbon atoms, hydroxyalkyl of 1 to 3 carbon atoms, phenyl, benzyl, substituted phenyl or substituted benzyl in which the substituents are hydroxy, halo, alkyl of 1 to 6 carbon atoms, alkoxy of 1 to 6 carbon atoms, trifluoromethyl, nitro, cyano, carbalkoxy of 2 to 7 carbon atoms, carboxamido, amino, alkylamino of 1 to 6 carbon atoms or dialkylamino of 2 to 12 carbon atoms;

R⁶ is phenyl, benzyl, 2-, 3-, or 4-pyridinyl, 2-pyrimidinyl or 2-pyrazinyl; any of which may be substituted by one or more hydroxy, halo, alkyl of 1 to 6 carbon atoms, alkoxy of 1 to 6 carbon atoms, trifluoromethyl, nitro, cyano, carbalkoxy of 2 to 7 carbon atoms, carboxamido, amino, alkylamino of 1 to 6 carbon atoms or dialkylamino of 2 to 12 carbon atoms;

and n is one of the integers 0, 1, 2, 3, 4 or 5; or a pharmaceutically acceptable salt thereof, with the proviso that when X is —CON(R⁷)— and R⁷ is alkyl, R⁶ is other than 2-pyrimidinyl.

8. A compound of claim 7 in which R² and R³, taken together, are tetramethylene, pentamethylene or hexamethylene.

9. A compound of claim 8 in which R⁴ is hydrogen and R⁵ is alkyl of 1 to 6 carbon atoms, phenyl or benzyl.

10. A compound of claim 8 in which R⁶ is 2-methoxyphenyl, 2-chlorophenyl or 2-pyrimidinyl.

11. The compound of claim 1 which is N-(1,1-dimethylethyl)-N¹-[4-[4-(2-methoxyphenyl)-1-piperazinyl]-butyl]urea, or a pharmaceutically acceptable salt thereof.

12. The compound of claim 1 which is N-[4-[4-(2-methoxyphenyl)-1-piperazinyl]butyl]-2,2-dimethylpropanamide, or a pharmaceutically acceptable salt thereof.

13. The compound of claim 1 which is 2,2-dimethylpropanoic acid 2-[4-(2-methoxyphenyl)-1-piperazinyl]ethyl ester, or a pharmaceutically acceptable salt thereof.

14. The compound of claim 1 which is 2,2-dimethylpropanoic acid 3-[4-(2-methoxyphenyl)-1-piperazinyl]propyl ester, or a pharmaceutically acceptable salt thereof.

15. The compound of claim 1 which is 2,2-dimethylpropanoic acid 3-[4-(2-chlorophenyl)-1-piperazinyl]propyl ester, or a pharmaceutically acceptable salt thereof.

16. The compound of claim 6 which is 2,2-dimethylpropanoic acid 3-[4-(2-pyrimidinyl)-1-piperazinyl]propyl ester, or a pharmaceutically acceptable salt thereof.

17. The compound of claim 1 which is (R)-N-[1-methyl-2-[4-(2-methoxyphenyl)-1-piperazinyl]ethyl]-trimethylacetamide, or a pharmaceutically acceptable salt thereof.

18. The compound of claim 1 which is N-2-(4-(2-methoxyphenyl)-1-piperazinyl)ethyl 2,2-dimethylpropanamide dihydrochloride, or a pharmaceutically acceptable salt thereof.

19. The compound of claim 1 which is N-(1,1-dimethylethyl)-4-(2-methoxyphenyl)-1-piperazineacetamide, or a pharmaceutically acceptable salt thereof.

20. The compound of claim 1 which is N-(1,1-dimethylethyl)-4-(2-pyrimidinyl)-1-piperazinepropanamide, or a pharmaceutically acceptable salt thereof.

21. The compound of claim 1 which is 2,2-dimethylpropanoic acid 2-[4-(2-pyrimidinyl)-1-piperazinyl]ethyl ester, or a pharmaceutically acceptable salt thereof.

22. The compound of claim 1 which is tertiary-butyl 3-[1-[4-(2-methoxyphenyl)piperazinyl]]-2-phenylpropanoate, or a pharmaceutically acceptable salt thereof.

23. The compound of claim 1 which is N-tertiary-butyl 3-[4-(2-methoxyphenyl)piperazinyl]-2-phenylpropanamide, or a pharmaceutically acceptable salt thereof.

24. The compound of claim 1 which is N-tertiary-butyl 2-[[4-(2-methoxyphenyl)piperazinyl]methyl]-3-phenylpropanamide or a pharmaceutically acceptable salt thereof.

25. The compound of claim 1 which is N-[2-[4-(2-methoxyphenyl)-1-piperazinyl)ethyl]-1-methylcyclohexanecarboxamide, or a pharmaceutically acceptable salt thereof.

26. The compound of claim 7 which is 4-(2-methoxyphenyl)-N-(1-methylcyclohexyl)-1-piperazinepropanamide, or a pharmaceutically acceptable salt thereof.

27. The compound of claim 7 which is 4-(2-pyrimidinyl)-N-(1-methylcyclohexyl)-1-piperazine-propanamide, or a pharmaceutically acceptable salt thereof.

28. The compound of claim 7 which is N-[2-[4-(2-methoxyphenyl)-1-piperazinyl]ethyl]-N'-(1-methylcyclohexyl)urea, or a pharmaceutically acceptable salt thereof.

29. The compound of claim 7 which is N-2-(4-(2-pyrimidinyl)-1-piperazinyl)ethyl-1-methylcyclohexyl-carboxamide, or a pharmaceutically acceptable salt thereof.

30. The compound of claim 7 which is (R)-N-[2-[4-(2-methoxyphenyl)-1-piperazinyl]-1-methylethyl]-1-methylcyclohexane carboxamide, or a pharmaceutically acceptable salt thereof.

31. The compound of claim 7 which is (R)-1-methyl-N-[1-methyl-2-[4-(2-pyrimidinyl)]-1-piperazinyl]ethyl]-cyclohexane carboxamide, or a pharmaceutically acceptable salt thereof.

32. The compound of claim 1 which is N-(1,1-dimethylethyl)-4-(2-methoxyphenyl)-1-piperazinyl-propanamide, or a pharmaceutically acceptable salt thereof.

33. The compound of claim 1 which is 2,2-dimethylpropanoic acid 2-(4-(2-methoxyphenyl)piperazin-1-yl)-1-phenylethyl ester, or a pharmaceutically acceptable salt thereof.

34. The compound of claim 1 which is O-(2-(4-(2-methoxyphenyl)piperazin-1-yl)ethyl)-N-(2-methyl-2-propyl)carbamate, or a pharmaceutically acceptable salt thereof.

35. The compound of claim 1 which is N-tert-butyl-2-methoxyphenyl-3-(4-(2-methoxyphenyl)-piperazin-1-yl)propanamide, or a pharmaceutically acceptable salt thereof.

36. The compound of claim 1 which is N-tert-butyl-3-[1-[4-(2-methoxy)phenyl]piperazinyl]-2-phenyl-propionhydrazide, or a pharmaceutically acceptable salt thereof.

37. The compound of claim 1 which is O-tert-butyl-3-[1-(4-(2-methoxy)phenyl)piperazinyl)-2-phenyl-propionohydroxamate, or a pharmaceutically acceptable salt thereof.

* * * * *